(12) United States Patent
Gliner et al.

(10) Patent No.: US 11,950,930 B2
(45) Date of Patent: Apr. 9, 2024

(54) MULTI-DIMENSIONAL ACQUISITION OF BIPOLAR SIGNALS FROM A CATHETER (71) Applicant: Biosense Webster (Israel) Ltd., Yokneam (IL)

(72) Inventors: Vadim Gliner, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 309 days.

(21) Appl. No.: 16/712,604

(22) Filed: Dec. 12, 2019

(65) Prior Publication Data

US 2021/0177356 A1 Jun. 17, 2021

(51) Int. Cl.
*A61B 5/367* (2021.01)
*A61B 5/00* (2006.01)
*A61B 5/287* (2021.01)
*A61B 5/341* (2021.01)
*A61B 5/349* (2021.01)

(52) U.S. Cl.
CPC ............ *A61B 5/6858* (2013.01); *A61B 5/287* (2021.01); *A61B 5/341* (2021.01); *A61B 5/349* (2021.01)

(58) Field of Classification Search
None
See application file for complete search history.

(56) References Cited

U.S. PATENT DOCUMENTS

| | | | |
|---|---|---|---|
| 4,699,147 A | 10/1987 | Chilson et al. | |
| 4,940,064 A | 7/1990 | Desai | |
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |

(Continued)

FOREIGN PATENT DOCUMENTS

| | | |
|---|---|---|
| CN | 111248993 A | 6/2020 |
| CN | 111248996 A | 6/2020 |

(Continued)

OTHER PUBLICATIONS

Extended European Search Report issued in Application No. 20 21 3554 dated Apr. 21, 2021.

*Primary Examiner* — Kennedy Schaetzle
(74) *Attorney, Agent, or Firm* — Troutman Pepper Hamilton Sanders LLP (57) ABSTRACT

Medical apparatus includes a probe with a basket assembly at its distal end, including a plurality of resilient spines with multiple electrodes arrayed along a length of each of the spines. Processing circuitry is configured to acquire a first bipolar electrical signal from the tissue between first and second electrodes at first and second locations along a first spine of the basket assembly, and to acquire a second bipolar electrical signal from the tissue between the first electrode and a third electrode in a third location on a second spine of the basket assembly, and to interpolate, based on the first and second bipolar electrical signals, a vectorial electrical property of the tissue along an axis that passes through the first location and between the second and third locations.

15 Claims, 2 Drawing Sheets

(56) References Cited

U.S. PATENT DOCUMENTS

| | | |
|---|---|---|
| 5,391,199 A | 2/1995 | Ben-Haim |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,433,198 A * | 7/1995 | Desai .................. A61B 5/7445 607/9 |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,239,724 B1 | 5/2001 | Doron et al. |
| 6,332,089 B1 | 12/2001 | Acker et al. |
| 6,428,537 B1 | 8/2002 | Swanson et al. |
| 6,456,864 B1 | 9/2002 | Swanson et al. |
| 6,484,118 B1 | 11/2002 | Govari |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,756,576 B2 | 7/2010 | Levin |
| 7,846,157 B2 | 12/2010 | Kozel |
| 7,848,787 B2 | 12/2010 | Osadchy |
| 7,869,865 B2 | 1/2011 | Govari et al. |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,456,182 B2 | 6/2013 | Bar-Tal et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,136,829 B2 | 11/2018 | Deno et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |

(56) References Cited

U.S. PATENT DOCUMENTS

| | | |
|---|---|---|
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0144510 A1 | 6/2011 | Ryu et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0126840 A1* | 5/2015 | Thakur .................. A61B 5/363 606/41 |
| 2015/0133919 A1 | 5/2015 | McDaniel et al. |
| 2015/0196215 A1 | 7/2015 | Laughner et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2015/0351652 A1* | 12/2015 | Marecki ............ A61B 18/1492 29/829 |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0331471 A1* | 11/2016 | Deno .................... A61B 34/20 |
| 2016/0338770 A1 | 11/2016 | Bar-Tal et al. |
| 2017/0027465 A1* | 2/2017 | Blauer ................ A61B 5/6858 |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235495 A1* | 8/2018 | Rubenstein .......... A61B 5/6859 |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0296111 A1 | 10/2018 | Deno et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |

(56) References Cited

U.S. PATENT DOCUMENTS

| | | |
|---|---|---|
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | WO 96/05768 A1 | 2/1996 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |

\* cited by examiner

MULTI-DIMENSIONAL ACQUISITION OF BIPOLAR SIGNALS FROM A CATHETER

FIELD OF THE INVENTION

The present invention relates generally to invasive diagnostic methods and apparatus, and particularly to catheter-based measurement of electrophysiological signals.

BACKGROUND

In electro-anatomical mapping of the heart, a catheter is inserted into a heart chamber, and electrodes on the catheter contact the myocardium within the chamber in order to acquire electrical signals at a large number of locations. A variety of specialized catheters, with arrays of electrodes extending over a distal portion of the catheter, have been developed in order to facilitate this process.

For example, U.S. Pat. No. 6,748,255, whose disclosure is hereby incorporated by reference herein in its entirety as though set forth in full, describes an improved basket catheter that is particularly useful for mapping the heart. The catheter comprises an elongated catheter body having proximal and distal ends and at least one lumen therethrough. A basket-shaped electrode assembly is mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body.

The catheter further comprises a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the spines of the basket-shaped mapping assembly to find the positions of the at least one electrode of each spine.

Catheters with multiple electrodes can be applied in making various sorts of diagnostic measurements. For example, U.S. Patent Application Publication 2019/0216346 describes a system including a catheter including multiple, spatially-distributed electrodes configured to measure electrical signals of a heart. The system is configured to determine a position of the electrodes at multiple, different catheter positions in the heart, and includes a processing unit, which maps electrical activity in the heart. The processing unit is configured to receive the measured electrical signals from each position of the multiple, different catheter positions and determine whether the measured electrical signals at the position are organized. If the measured electrical signals at the position are organized, the processing unit is configured to determine at least one of velocity vectors, cycle length, and degree of organization at the position from the measured electrical signals.

SUMMARY

Embodiments of the present invention that are described hereinbelow provide improved methods and systems for electrophysiological measurement and mapping.

There is therefore provided, in accordance with an embodiment of the invention, medical apparatus, including a probe, which includes an insertion tube configured for insertion into a body cavity of a patient, and a basket assembly connected distally to the insertion tube. The basket assembly includes a plurality of resilient spines having respective proximal and distal tips and including multiple electrodes arrayed along a length of each of the spines between the respective proximal and distal tips. The proximal tips of the spines are joined at a proximal end of the basket assembly, and the distal tips of the spines are joined at a distal end of the basket assembly, and the spines bow radially outward when the basket assembly is deployed in the body cavity, whereby the electrodes contact tissue in the body cavity. Processing circuitry is configured to acquire a first bipolar electrical signal from the tissue between first and second electrodes at first and second locations along a first spine of the basket assembly, and to acquire a second bipolar electrical signal from the tissue between the first electrode and a third electrode in a third location on a second spine of the basket assembly, and to interpolate, based on the first and second bipolar electrical signals, a vectorial electrical property of the tissue along an axis that passes through the first location and between the second and third locations.

In some embodiments, the second electrode is adjacent to the first electrode on the first spine, and the second spine is adjacent to the first spine. In one embodiment, among the electrodes on the second spine, the third electrode is closest to the first electrode.

Additionally or alternatively, the processing circuitry is configured to derive a longitudinal component of the vectorial electrical property from the first bipolar electrical signal, and a transverse component of the vectorial electrical property from the second bipolar signal. In a disclosed embodiment, the processing circuitry is configured to find an amplitude and a direction of the vectorial electrical property by computing a vector sum of the longitudinal and transverse components.

In one embodiment, the first and second bipolar signals arise due to an electrical activation wave passing through the tissue, and the vectorial electrical property includes a velocity of the electrical activation wave. Alternatively or additionally, the vectorial electrical property includes a simulated bipolar electrical signal between the first location and a fourth location on the axis that passes through the first location and between the second and third locations.

In some embodiments, the processing circuitry is configured to map the vectorial electrical property over an area of the tissue that is contacted by the electrodes on the basket assembly. Typically, the apparatus includes one or more position sensors connected to the probe and configured to output position signals that are indicative of a position of the basket assembly, wherein the processing circuitry is configured to process the position signals in order to find location coordinates of the first, second and third locations, and to apply the location coordinates in mapping the vectorial electrical property.

In a disclosed embodiment, the insertion tube includes a flexible catheter configured for insertion into a chamber of a heart of the patient, and the electrodes are configured to sense electrical potentials in myocardial tissue within the chamber.

There is also provided, in accordance with an embodiment of the invention, a method for medical diagnosis, which includes providing a probe that is configured for insertion into a body cavity of a patient and includes a basket assembly including a plurality of resilient spines having respective proximal and distal tips and including multiple electrodes arrayed along a length of each of the spines between the respective proximal and distal tips. The proximal tips of the spines are joined at a proximal end of the basket assembly, and the distal tips of the spines are joined at a distal end of the basket assembly, and the spines bow radially outward when the basket assembly is deployed in the body cavity, whereby the electrodes contact tissue in the body cavity. A first bipolar electrical signal in the tissue is acquired between first and second electrodes at first and second locations along a first spine of the basket assembly. A second bipolar electrical signal in the tissue is acquired between the first electrode and a third electrode in a third location on a second spine of the basket assembly. Based on the first and second bipolar signals, a vectorial electrical property of the tissue is interpolated along an axis that passes through the first location and between the second and third locations.

The present invention will be more fully understood from the following detailed description of the embodiments thereof, taken together with the drawings in which:

DETAILED DESCRIPTION OF EMBODIMENTS

Basket catheters are useful in rapidly collecting large amounts of electrical data from tissue within body cavities, and specifically from myocardial tissue in the chambers of the heart. Among the measurements that are commonly made using such catheters are bipolar measurements of electrical potentials in the tissue, which are acquired between adjacent electrodes on a given spine. These bipolar measurements give an indication, inter alia, of the propagation of electrical activation waves through the tissue. Only the component of the propagation along the direction parallel to the spine can be measured in this manner, however, and components perpendicular to the spine may be missed.

Embodiments of the present invention that are described herein offer a solution to this problem, which enables a basket catheter to be used in measuring vectorial electrical properties of the tissue, along axes that are angled relative to the spines, i.e., at perpendicular and oblique angles relative to the longitudinal axes of the spines. These properties may include, for example, the directional velocity of the local activation wave in the tissue, as well as simulated bipolar signals between an electrode on one of the spines and a location where there is no physical electrode.

In the disclosed embodiments, processing circuitry associated with the basket catheter implements these capabilities by acquiring bipolar signals both from pairs of electrodes on the same spine and from pairs of electrodes on different spines (typically, neighboring spines, although not necessarily). Different pairs of electrodes may be chosen in order to optimize the bipolar signals that are acquired, in terms of amplitude and direction. By combining bipolar signals between an electrode and its neighbor along the spine, and between the electrode and a neighbor on an adjacent spine, the processing circuitry is able to emulate the operation of an omnidirectional bipolar probe, notwithstanding the constraints imposed by the structure of the basket assembly.

In the embodiments that are described herein, medical apparatus comprises a probe, which comprises an insertion tube configured for insertion into a body cavity of a patient. A basket assembly, connected distally to the insertion tube, comprises multiple resilient spines, with multiple electrodes arrayed along the length of each of the spines. The proximal tips of the spines are joined at the proximal end of the basket assembly, and the distal tips of the spines are joined at the distal end of the basket assembly, so that the spines bow radially outward when the basket assembly is deployed in the body cavity. The electrodes thus contact tissue in the body cavity.

Processing circuitry, such as a programmable processor in the apparatus, acquires a first bipolar electrical signal from the tissue between first and second electrodes along a first spine of the basket assembly, and acquires a second bipolar electrical signal from the tissue between the first electrode on the first spine and a third electrode on a second spine of the basket assembly. The processing circuitry can then interpolate a vectorial electrical property of the tissue based on the first and second bipolar signals. In some cases, the vectorial electrical property will be directed longitudinally along the spine or along the transverse direction between the first and third electrodes. More generally, however, the vectorial electrical property will have both longitudinal and transverse components, and will thus be directed along an axis that passes through the location of the first electrode and between the locations of the second and third electrodes.

The embodiments that are described hereinbelow relate specifically to a basket catheter that is used in sensing electrical potentials in myocardial tissue in a chamber of the heart. The principles of the present invention, however, may similarly be applied in making other sorts of electrophysiological measurements in other body cavities.

Figure 1:
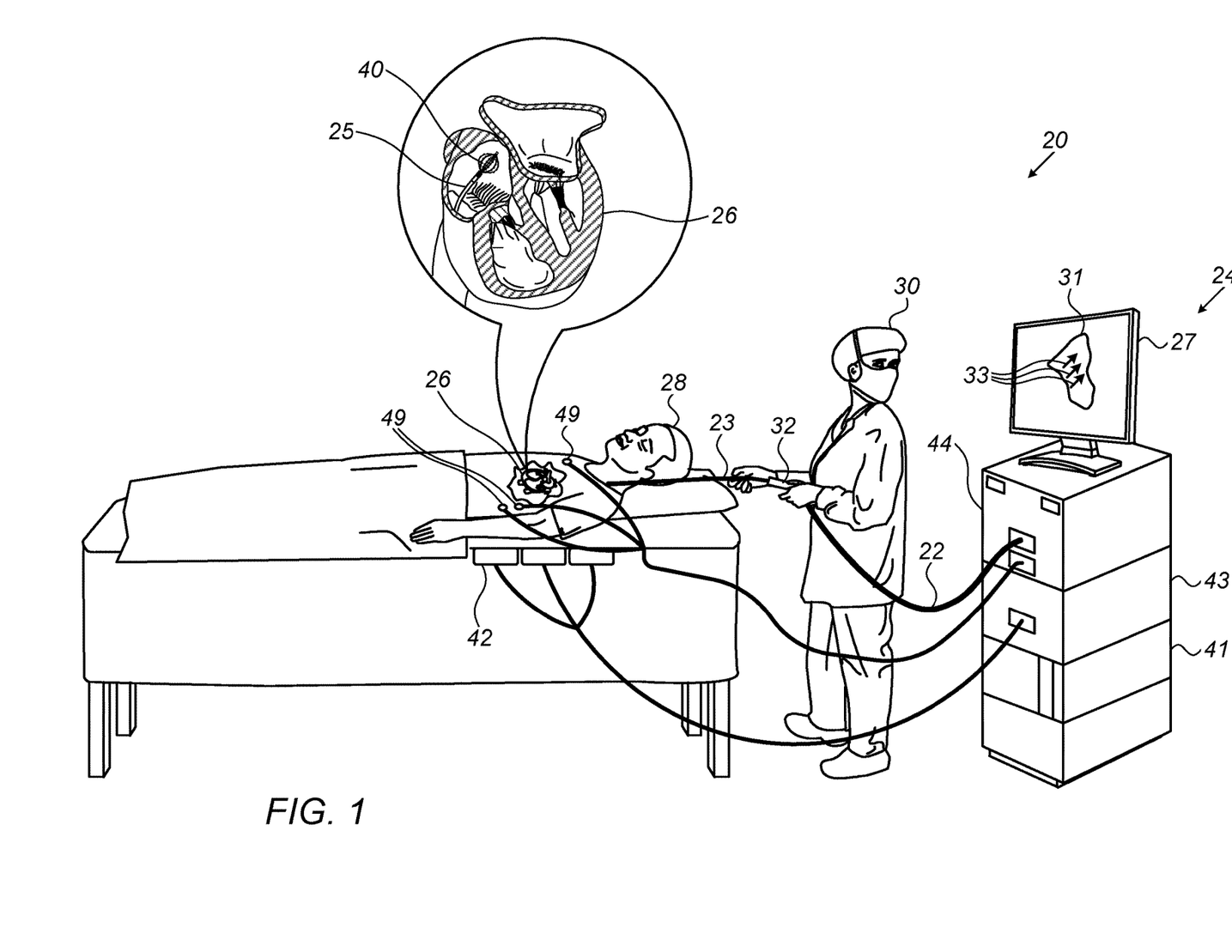
FIG. 1 is a schematic, pictorial illustration of a system for electro-anatomical mapping, in accordance with an embodiment of the invention.
Figure 2:
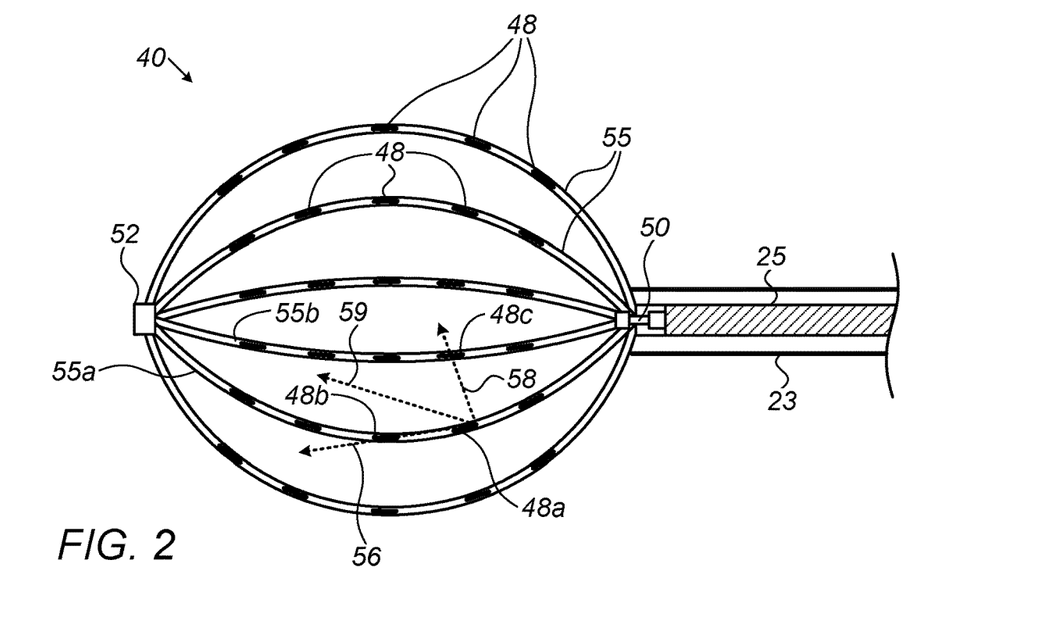
FIG. 2 is a schematic side view of a basket catheter, in accordance with an embodiment of the invention.

Reference is now made to FIGS. 1 and 2, which schematically illustrate an electro-anatomical mapping system 20 using a basket catheter 22, in accordance with an embodiment of the invention. FIG. 1 is a pictorial view of the system as a whole, while FIG. 2 shows details of a basket assembly 40 at the distal end of catheter 22. Elements of system 20 may be based on components of the CARTO® system, produced by Biosense Webster, Inc. (Irvine, Calif.).

A physician 30 navigates catheter 22 so as to deploy basket assembly 40 in a target location in a chamber of a heart 26 of a patient 28. Basket assembly 40 is connected distally to an insertion tube 25, which physician 30 steers using a manipulator 32 near the proximal end of catheter 22. Basket assembly 40 is inserted in a collapsed configuration through a sheath 23, via the vascular system of patient 28, into the heart chamber that is to be mapped, and is then deployed from the sheath and allowed to expand within the chamber. By containing basket assembly 40 in this collapsed configuration, sheath 23 also serves to minimize vascular trauma along the way to the target location.

As can be seen in FIG. 2, basket assembly 40 comprises a plurality of resilient spines 55, with multiple electrodes 48 arrayed along the length of each of the spines. Spines 55 typically comprise a suitable, resilient metal or plastic material, for example. The proximal tips of spines 55 are joined at the proximal end of the basket assembly, where the basket assembly connects to the distal end of insertion tube 25. The distal tips of spines 55 are likewise joined together at the distal end of the basket assembly. The spines bow radially outward when basket assembly 40 is deployed from sheath 23 into the heart chamber. Physician 30 then manipulates catheter 22 so that electrodes 48 contact the myocardial tissue in the heart chamber. Basket assembly 40 may comprise other components, as well (not shown in the figures), such as ultrasound transducers, contact force sensors, and temperature sensors. Electrodes 48, as well as these other components, are connected to wires (not shown) running through insertion tube 25 to the proximal end of catheter 22, where they connect to processing circuitry in a console 24.

Catheter 22 comprises one or more position sensors, which output position signals that are indicative of the position (location and orientation) of basket assembly 40. In the embodiment shown in FIG. 2, basket assembly 40 incorporates a magnetic sensor 50 at the distal end of insertion tube 25, or equivalently, at the proximal end of the basket assembly. A second magnetic sensor 52 is fixed to the distal end of the basket assembly. Alternatively, basket assembly 40 may comprise only a single magnetic sensor or may comprises two or more magnetic sensors at different locations on the basket assembly. Magnetic sensors 50 and 52 typically comprise miniature coils or Hall effect devices, for example, which output electrical signals in response to an applied magnetic field. Like electrodes 48, magnetic sensors 50 and 52 are connected to console 24 via wires running through insertion tube 25.

Patient 28 is placed in a magnetic field generated by magnetic field generator coils 42, which are driven by a drive circuit 43 in console 24 to produce multiple magnetic field components directed along different, respective axes. During navigation of basket assembly 40 in heart 26, magnetic sensors 50, 52 output signals in response to these magnetic field components. Position sensing circuitry, such as a processor 41 in console 24, receives these signals via interface circuits 44, and processes the signals in order to find the location and orientation coordinates of basket assembly 40, and thus of each of electrodes 48. Interface circuits 44 comprise suitable analog amplifiers and filters, as well as analog/digital converters, for processing the signals output by both sensors 50, 52 and electrodes 48 and input corresponding digital values to processor 41.

The methods and apparatus for magnetic position sensing that are implemented in system 20 are based on those that are used in the above-mentioned CARTO® system. The principles of operation of this sort of magnetic sensing are described in detail, for example, in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all hereby incorporated by reference herein in their entireties as though set forth in full with a copy in the attached Appendix. Alternatively, system 20 may implement other magnetic position sensing technologies that are known in the art.

Further alternatively or additionally, system 20 may apply other position-sensing technologies in order to find the coordinates of electrodes 48 on basket assembly 40. For example, processor 41 may sense the impedances between electrodes 48 and body-surface electrodes 49, which are applied to the chest of patient 28, and may convert the impedances into location coordinates using techniques that are known in the art. By using the aforementioned measured impedances from electrodes 48, location of the electrodes 48 can be determined by, for example, the CARTO™ system, produced by Biosense-Webster (Irvine, Calif.) and is described in detail in U.S. Pat. Nos. 7,756,576, 7,869,865, 7,848,787, and 8,456,182, whose disclosures are all incorporated herein by reference with a copy provided in the Appendix. This method is sometimes called Advanced Catheter Location (ACL). In this case, electrodes 48 themselves serve as position sensors for ACL.

Processor 41 uses the spatial and electrophysiological signals that it receives via interface circuits 44 in constructing an electro-anatomical map 31 of the heart chamber in which basket assembly 40 is deployed. During and/or following the procedure, processor 41 may render electro-anatomical map 31 to a display 27. In the embodiment that is shown in FIG. 1, processor 41 superimposes one or more icons 33, which indicate a vectorial electrical property of the myocardial tissue that the processor derives from bipolar electrical signals that it receives from basket assembly 40. Techniques that may be applied by the processor in deriving such vectorial properties are described further hereinbelow.

In some embodiments, processor 41 comprises a general-purpose computer, with suitable interface circuits 44 for receiving signals from catheter 21 (including low-noise amplifiers and analog/digital converters), as well as for receiving signals from and controlling the operation of the other components of system 20. Processor 41 typically performs these functions under the control of software stored in a memory 48 of system 20. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables the processor to perform the methods of signal acquisition and processing that are described below. Additionally or alternatively, at least some of the functions of processor 41 may be carried out by dedicated or programmable hardware logic.

The system configuration that is shown in FIG. 1 is chosen by way of example for the sake of conceptual clarity. For the sake of simplicity, FIG. 1 shows only the elements of system 20 that are specifically related to the disclosed techniques. The remaining elements of the system will be apparent to those skilled in the art, who will likewise understand that the principles of the present invention may be implemented in other medical diagnostic systems, using other components. All such alternative implementations are considered to be within the scope of the present invention.

Figure 3:
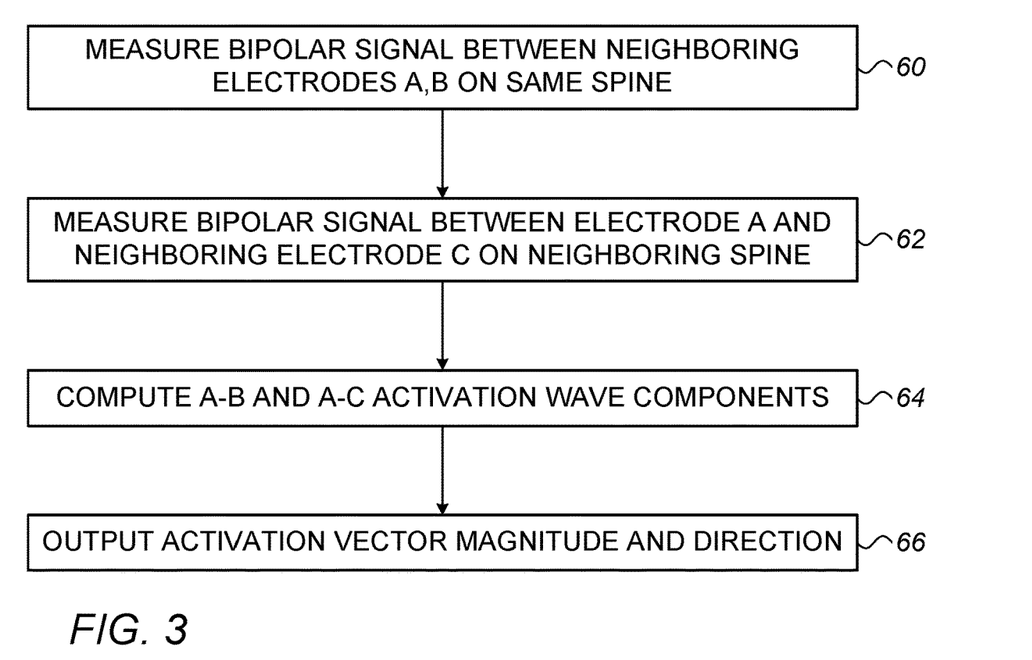
FIG. 3 is a flow chart that schematically illustrates a method for acquiring and processing electrophysiological signals, in accordance with an embodiment of the invention.

FIG. 3 is a flow chart that schematically illustrates a method for acquiring and processing electrophysiological signals, in accordance with an embodiment of the invention. The method is described, for the sake of clarity and concreteness, with reference to the elements of system 20, and particularly basket assembly 40, as shown in FIG. 2. This method represents the algorithm applied by processor 41 (FIG. 1) in deriving vectorial electrical properties of the myocardial tissue contacted by the basket assembly. As noted above, however, other implementations of the principles of this method are also considered to be within the scope of the present invention.

Processor 41 acquires a first bipolar electrical signal from the myocardial tissue between neighboring electrodes 48*a* and 48*b* on a first spine 55*a*, at a first bipolar acquisition step 60. Alternatively, electrodes 48*a* and 48*b* may be spread apart at a greater distance along spine 55*a*. The locations of electrodes 48*a* and 48*b*, in contact with the myocardial tissue, define a longitudinal axis 56, running for a portion of the axis 56 along spine 55*a*.

Processor 41 also acquires a second bipolar electrical signal between electrode 48*a* and an electrode 48*c*, which is located on an adjacent spine 55*b*, at a second bipolar acquisition step 62. Alternatively, spine 55*b* may be non-adjacent to spine 55*a*, as long as both spines are in contact with the myocardial tissue. Electrode 48c may conveniently be chosen as the closest electrode on spine 55b to electrode 48a. The locations of electrodes 48a and 48c define a transverse axis 58, which is perpendicular to or obliquely oriented relative to longitudinal axis 56. Alternatively or additionally, processor 41 may acquire the bipolar electrical signals between electrode 48a and other electrodes on spine 55b or on other spines.

Based on the bipolar electrical signals acquired at steps 60 and 62, processor 41 computes vector components of electrical potentials propagating in the myocardial tissue, at a component computation step 64. In the present example, the processor computes components of an activation wave, including a longitudinal (A-B) component along axis 56 and a transverse (A-C) component along axis 58. These directional components are derived from the bipolar signals acquired respectively at steps 60 and 62. Processor 41 interpolates between these components in order to find the magnitude and direction of the activation vector, at a vector computation step 66. The result is a vector sum, with a direction passing between the locations of electrodes 48b and 48c, for example along an oblique axis 59 passing through the location of electrode 48a, as shown in FIG. 2.

This vector sum represents the local, directional velocity of the electrical activation wave in the myocardial tissue at the location of electrode 48a. Processor 41 typically makes similar measurements, using bipolar electrode pairs along and between spines 55, at other electrode locations on basket assembly 40. The processor is thus able to generate map 31 (as shown in FIG. 1) including icons 33 representing the activation velocity—as well as other vectorial electrical properties—over the inner surface of the heart chamber in which basket assembly 40 is deployed.

Alternatively or additionally, processor 41 may generate and display the vectorial electrical property in terms of simulated bipolar electrical signals, based on the bipolar signals acquired respectively at steps 60 and 62. For example, processor 41 may generate such a simulated signal between electrode 48a and a "virtual electrode" at a location on axis 59. The magnitudes of these simulated signal bipolar signals may be computed with or without computation of a corresponding direction. In one embodiment, the magnitude of the simulated bipolar signal at any given point is approximated simply as the sum of the amplitudes of the bipolar signals acquired respectively at steps 60 and 62. As used herein, the term "vectorical electrical property" includes any electrical signal generated by organ tissues (e.g., cardiac) in which physical characteristics (e.g., volts or amperes) as well as directional characteristics can be derived from such signals obtained from specified electrodes 48. Such property may include, as discussed earlier, directional velocity of the local activation wave in the tissue as measured by the electrodes 48, as well as simulated bipolar signals between an electrode on one of the spines and a location where there is no physical electrode.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
   a probe, comprising:
   an insertion tube configured for insertion into a body cavity of a patient; and
   a basket assembly connected distally to the insertion tube and comprising a plurality of resilient spines having respective proximal and distal tips and comprising multiple electrodes arrayed along a length of each of the spines between the respective proximal and distal tips, such that the proximal tips of the spines are joined at a proximal end of the basket assembly, and the distal tips of the spines are joined at a distal end of the basket assembly, and the spines bow radially outward when the basket assembly is deployed in the body cavity, whereby the electrodes contact tissue in the body cavity; and
   processing circuitry, which is configured to acquire a first bipolar electrical signal from the tissue between first and second electrodes at first and second locations along a first spine of the basket assembly, the second electrode being adjacent to the first electrode on the first spine, and to acquire a second bipolar electrical signal from the tissue between the first electrode and a third electrode in a third location on a second spine of the basket assembly adjacent to the first spine, the third electrode being closest to the first electrode among electrodes on the second spine, a first axis between the first electrode and the third electrode extending at an oblique angle relative to a second axis extending between the first electrode and the second electrode, and to interpolate, based on the first and second bipolar electrical signals, a vectorial electrical property of the tissue along a third axis that passes through the first location and between the second and third locations.

2. The apparatus according to claim 1, wherein the processing circuitry is configured to derive a longitudinal component of the vectorial electrical property from the first bipolar electrical signal, and a transverse component of the vectorial electrical property from the second bipolar signal.

3. The apparatus according to claim 2, wherein the processing circuitry is configured to find an amplitude and a direction of the vectorial electrical property by computing a vector sum of the longitudinal and transverse components.

4. The apparatus according to claim 1, wherein the first and second bipolar signals arise due to an electrical activation wave passing through the tissue, and the vectorial electrical property comprises a velocity of the electrical activation wave.

5. The apparatus according to claim 1, wherein the processing circuitry is configured to map the vectorial electrical property over an area of the tissue that is contacted by the electrodes on the basket assembly.

6. The apparatus according to claim 5, and comprising one or more position sensors connected to the probe and configured to output position signals that are indicative of a position of the basket assembly, wherein the processing circuitry is configured to process the position signals in order to find location coordinates of the first, second and third locations, and to apply the location coordinates in mapping the vectorial electrical property.

7. The apparatus according to claim 1, wherein the insertion tube comprises a flexible catheter configured for insertion into a chamber of a heart of the patient, and the electrodes are configured to sense electrical potentials in myocardial tissue within the chamber.

8. The apparatus of claim 1, wherein the processing circuitry is further configured to approximate a magnitude of the simulated bipolar signal at the fourth location by calculating a sum of the first bipolar electrical signal and the second bipolar electrical signal.

9. A method for medical diagnosis, comprising:

providing a probe that is configured for insertion into a body cavity of a patient and comprises a basket assembly comprising a plurality of resilient spines having respective proximal and distal tips and comprising multiple electrodes arrayed along a length of each of the spines between the respective proximal and distal tips, such that the proximal tips of the spines are joined at a proximal end of the basket assembly, and the distal tips of the spines are joined at a distal end of the basket assembly, and the spines bow radially outward when the basket assembly is deployed in the body cavity, whereby the electrodes contact tissue in the body cavity; and acquiring a first bipolar electrical signal in the tissue between first and second electrodes at first and second locations along a first spine of the basket assembly, the second electrode being adjacent to the first electrode on the first spine;

acquiring a second bipolar electrical signal in the tissue between the first electrode and a third electrode in a third location on a second spine of the basket assembly adjacent to the first spine, the third electrode being closest to the first electrode among electrodes on the second spine, a first axis between the first electrode and the third electrode extending at an oblique angle relative to a second axis extending between the first electrode and the second electrode; and interpolating, based on the first and second bipolar signals, a vectorial electrical property of the tissue along a third axis that passes through the first location and between the second and third locations.

10. The method according to claim 9, wherein interpolating the vectorial electrical property comprises deriving a longitudinal component of the vectorial electrical property from the first bipolar electrical signal, and a transverse component of the vectorial electrical property from the second bipolar signal.

11. The method according to claim 10, wherein interpolating the vectorial electrical property comprises finding an amplitude and a direction of the vectorial electrical property by computing a vector sum of the longitudinal and transverse components.

12. The method according to claim 9, wherein the first and second bipolar signals arise due to an electrical activation wave passing through the tissue, and the vectorial electrical property comprises a velocity of the electrical activation wave.

13. The method according to claim 9, and comprising mapping the vectorial electrical property over an area of the tissue that is contacted by the electrodes on the basket assembly.

14. The method according to claim 13, and comprising receiving position signals that are indicative of a position of the basket assembly, and processing the position signals in order to find location coordinates of the first, second and third locations, wherein mapping the vectorial electrical property comprises applying the location coordinates in mapping the vectorial electrical property.

15. The method according to claim 9, wherein acquiring the first and second bipolar signals comprises inserting a flexible catheter into a chamber of a heart of the patient, and deploying the basket assembly from the catheter in order to sense electrical potentials in myocardial tissue within the chamber.

* * * * *